United States Patent [19]

De Lasa et al.

[11] Patent Number: 5,740,291

[45] Date of Patent: Apr. 14, 1998

[54] FIBER OPTIC SENSOR FOR SENSING PARTICLE MOVEMENT IN A CATALYTIC REACTOR

[75] Inventors: Hugo L De Lasa; Brad J. Young; Stefan Krol, all of London, Canada

[73] Assignee: The University of Western Ontario, Canada

[21] Appl. No.: 543,197

[22] Filed: Oct. 13, 1995

[51] Int. Cl.$^6$ .................................................. G01N 21/49
[52] U.S. Cl. .................. 385/31; 385/33; 250/227.11; 250/227.24; 250/574; 356/342
[58] Field of Search ................ 385/31, 27, 33, 385/34; 356/342; 250/222.2, 227.11, 227.24, 574; 73/61.71, 28.01

[56] References Cited

U.S. PATENT DOCUMENTS

| | | | |
|---|---|---|---|
| 3,940,608 | 2/1976 | Kissinger et al. | |
| 4,659,218 | 4/1987 | de Lasa et al. | |
| 4,722,599 | 2/1988 | Fruengel et al. | 356/342 |
| 4,834,493 | 5/1989 | Cahill et al. | |
| 4,953,947 | 9/1990 | Bagavatula | 385/31 |
| 5,124,130 | 6/1992 | Costello et al. | |
| 5,155,549 | 10/1992 | Dhadwal | 356/342 |
| 5,265,465 | 11/1993 | Thomas | |
| 5,270,222 | 12/1993 | Moslehi | |
| 5,315,609 | 5/1994 | Tanaka et al. | 385/34 |
| 5,359,683 | 10/1994 | Pan | 385/34 |
| 5,416,869 | 5/1995 | Yoshino | 385/34 |

FOREIGN PATENT DOCUMENTS 61-182554  8/1986  Japan ..................... 356/342

OTHER PUBLICATIONS

"Modelling turbulent fluidized bed reactors: tracer and fibre optic probe studies", by P. Ege, et al; The Chemical Engineering Journal 61 (1996) 179–190 (no month).

"New fiber–optic method for measuring velocities of strands and solids hold–up in gas–solids downflow reactors", by D.A. Sobocinski, et al, Power Technology 83 (1995) 1–11 (Feb.).

"Investigation Of The Flow Structure In Turbulent Fluidized Beds", by Paul Edward Ege, Department of Chemical Engineering, Norwegian Institute of Technology, The University of Trondheim, N 7034 Trondheim NTH, Norway, pp. 39–56 (Jan. 1995).

Young et al., Abstract No. 9h30, Novel CREC–GS–Optiprobe, Fluid Dynamics Studies in Down Flow Reactors, Programme Complet 45$^{ieme}$ Congress de la SCGCh, Oct. 1995.

D.A. Krohn, Intensity Modulated Fiber Optic Sensors Overview, SPIE vol. 718 Fiber Optic and Laser Sensors IV (1986). (no month available).

P. Ege et al., Modeling Turbulent Fluidized Bed Reactors Tracer and Fibre Optic Probes Studies, Chemical Engineering Journal, 1994 Sep.

*Primary Examiner*—Rodney B. Bovernick
*Assistant Examiner*—Yisun Song
*Attorney, Agent, or Firm*—Bell Seltzer Intellectual Property Law Group of Alston & Bird, LLP

[57] ABSTRACT

An optical probe for sensing presence of small moving particles passing through a defined sensing region comprises:

i) an emitter optic fiber for transmitting from its tip radiant energy outwardly of the probe;

ii) a receptor optic fiber for receiving radiant energy reflected by such particles moving through said sensing region;

iii) a lens for focusing radiant energy emitted from the emitter tip into a focal region, spaced outwardly of the probe and which diverges outwardly into a defined high density radiant energy region;

iv) the receptor optic fiber defining a diverging viewing region projecting outwardly towards the high density radiant energy region, the receptor optic fiber being positioned relative to the lens to project the viewing region to overlap a useful portion of the high density radiant energy region to define thereby the sensing region. This sensor is particularly useful in monitoring the flow characteristics of catalytic particles in a catalytic reactor for cracking of gasoline constituents.

27 Claims, 11 Drawing Sheets

Profile of SELFOC GRIN Lens

FIBER OPTIC SENSOR FOR SENSING PARTICLE MOVEMENT IN A CATALYTIC REACTOR

FIELD OF THE INVENTION

This invention relates to an optical probe for sensing presence of small moving particles passing through a defined sensing region and more particularly to the sensing of catalytic particle velocity and concentrations in a catalytic reactor.

BACKGROUND OF THE INVENTION

Catalyst circulation rates in industrial fluid catalytic cracking units in modern refineries are surprisingly still poorly controlled due to the lack of reliable industrial type sensors which can determine local catalytic particle concentration, local catalytic particle and/or catalytic particle cluster velocities as well as withstand the extreme environment which exists in this type of industrial reactor. The control of catalytic particle circulation is very important from numerous stand points which include the provision of a close monitoring of the thermal balance of the fluid catalytic cracking unit and for securing higher yields of desired products such as the gasoline fraction.

Given the increasing need for producing higher levels of olefins in gasoline with low levels of aromatics such as benzene and toluene, olefins can be alkylated later on producing larger quantities of environmentally acceptable gasoline isoparaffins. Hence the better the production, by catalytic cracking of the olefins in gasoline, the more environmentally friendly is the resultant product. It should be noted that sensors which might be used for measuring characteristics of catalytic flow in the reactors may also become a critical factor for the implementation of the other types of chemical processes such as manufacture of synthesis gas, hydrogen from natural gas and oxygenate production, for example, methanol, higher alcohols, methyl terbutylether and ethyl terbutylether. It is also appreciated that flow behaviour information (normally in terms of particle concentration and particle velocity) is valuable in controlling other types of chemical processes such as those involving pneumatic transport or spray drying as encountered in processing minerals, manufacturing pharmaceuticals and food products.

It should be understood that in referring to an evaluation of particle characteristics in a reactor system, the particles need not necessarily be solid, instead particle as used in the description of this application, refers to any discreet entity which is a different phase than the other medium, for example, gas bubbles in a liquid or fluidized bed media would constitute particles, oil mycels in an aqueous solution would constitute particles, water vapor droplets in a moving gas stream would constitute particles and solid catalytic particles moving in a liquid stream would also constitute particles.

A variety of intrusive and non-intrusive sensors are available for sensing velocity of the phases both, axially and radial profiles, hold up of the phases, solid circulation rate and the like. Intrusive sensors to some extent disturb the flow of the fluid in which the particle characteristics are to be monitored, whereas, non-intrusive sensors do not effect the flow patterns. However, it is difficult to sample particle information in the middle of the reactor when the sensor is non-intrusive.

Fibre optics have created considerable interest as used in a variety of sensors including the medical community. Fibre optics allow the location of probes in very remote areas where miniaturization is particularly important. Sensors which involve fibre optics are normally referred to as extrinsic and intrinsic sensors. The extrinsic sensors may be grouped into three families of absorption, reflection or refraction/reflection type probes. Normally sensors of this type tend to be quite intrusive in respect of effecting flow of material over the sensors. An example of a refractive/reflective type of sensor is described in U.S. Pat. No. 4,659,218. A sensor involving the use of fibre optics determines one or more physical characteristics of individual bubbles in a gas liquid system or a gas liquid solid system at reactor temperature and pressures. The fibre optic probe has a rounded end portion projecting into the reactor where a source of incident light is directed on to the probe. The rounded end portion of the probe is formed with a radius of curvature sufficiently large whereby the angle of incidence of the source light at the rounded portion is greater than the angle of total reflection for the fibre optic when in contact with gas. The angle of incidence is less than the angle of total reflection for the fibre optic when in contact with the liquid. By virtue of this difference, and resultant change in light intensities of the reflected light emerging from the probe, an evaluation of bubble characteristics can be made. Another type of fibre optic sensor involves reflection where emitted light, reflected from an object, is gathered by the same fibre optic or one or more receptor fibre optics. An example, of this type of system is described in U.S. Pat. No. 3,940,608. A fibre optic bundle has a plurality of emitter fibres and receptor fibres. The emitter fibres transmit light from a suitable light source to a lens configuration which focuses the light emitted from the emitter fibres, by a projection type focal lens, where the focal region for the image can be in the range of 0.4 inches or greater.

Krone (1984), "Fibre Optic Displacement Sensors", Proceedings of the ISA Houston Tex., Vol. 39, part 1, page 331-340, describes fibre optic displacement sensors for use in factory automation systems. The fibre optic displacement sensors are particularly useful in sensing when a rather large flat or curved surface moves towards or away from the sensor, for example, in sensing rotation of parts, parts cleaning, film thicknesses, eccentricity, shaft run out vibration, axial motion, proximity, concentricity, diameter, alignment, thickness and cerval positioning. The sensor is similar to that described in U.S. Pat. No. 3,940,608. However, a lens is used to provide a focal region which may be one to three inches from the sensor. This considerably extends the dynamic region for sensing and hence broadens the use of the sensor in sensing the movement of the various types of items above described. It is noted in this article that by use of various optical configurations of the fibres as well as lenses, allows the sensors to function over a distance of up to five inches, by having a accuracy in the range of 0.001 inches in detecting displacement of the object being sensed.

Krone Intensity Modulated Fibre Optics Sensors overview, SPIE, Vol. 718, Fibre Optic and Laser Sensors IV, 1986, 2–11, describes various fibre optic sensor configurations, where the reflective type of fibre optics may include coaxial, hemispherical, random, single or fibre pairs. As further noted in this article and in keeping with Krone's earlier article, by use of an appropriate lens system, the dynamic range for detecting position of an object, can be expanded from 0.2 inches to 5 inches or more. In view of this long range for the sensors, it is suggested that the light energy emitted by the fibre optics may be used in remote fibre fluorometry for chemical analysis. Typically, a high intensity light beam is transmitted through the optic fibre to a sample material. When the target material is excited by the light beam, it emits a characteristic fluorescent emission which is received and carried back along the same fibre for transmitting the initial light. A computer aided detector may then be used in conjunction with analyzing the fluorescent emission. If there is a delay in the time after excitation of the target material and the emission of fluorescence, the transmitting of the fluorescent signal back to the same fibre is particularly useful.

SUMMARY OF THE INVENTION

None of these prior art systems answer the need for detecting on a reliable consistent basis, particle velocity and particle concentration in a fluid moving system. This my be partly due to inappropriate illuminated regions in which the detection can take place, use of bulky lens systems to focus light for the illuminated region a considerable distance from the sensor and misunderstandings about the purpose of the lens focused region and the angle of incidence to provide for reflection from particles travelling through the focal region.

The sensing probe in accordance with various aspect of this invention deal with these problems and provide a sensor which is more than capable of sensing the presence of small moving particles through a sensing region.

In accordance with an aspect of the invention, an optical probe for sensing presence of small moving particles passing through a defined sensing region comprises:

i) an emitter optic fibre for transmitting from its tip radiant energy outwardly of the probe;

ii) a receptor optic fibre for receiving radiant energy reflected by such particles moving through said sensing region;

iii) a lens for focusing radiant energy emitted from the emitter tip into a focal region, spaced outwardly of the probe and which radiant energy diverges outwardly from said focal region into a defined high density radiant energy region;

iv) the receptor optic fibre defining a diverging viewing region projecting outwardly towards the high density radiant energy region, the receptor optic fibre being positioned relative to the lens to project the viewing region to overlap a useful portion of the high density radiant energy region to define thereby the sensing region.

In accordance with another aspect of the invention, an apparatus for detecting presence of small catalytic particles passing through a defined sensing region in a catalytic reactor, to determine catalyst particle velocities and particle concentrations in the reactor, comprises:

i) an optical probe for sensing catalytic particles passing through the sensing region;

ii) a laser emitting monochromatic light of an energy and wave length which is reflected by small catalytic particles in the fluid stream;

iii) a first fibre optic for transmitting the light from the laser to the probe;

iv) a second fibre optic for receiving light reflected by catalytic particles passing through the sensing region;

v) the optical probe when positioned in a catalytic reactor disrupting flow of the phases to define adjacent the probe a flow disruption region, and outwardly beyond the flow disruption region a non-disrupted flow region;

vi) the first fibre optic terminating in an emitter tip and the second fibre optic terminating in a receiver tip where the emitter tip is positioned adjacent the receiver tip, the second fibre optic transmitting receive reflected light to a light detector which generates signals proportional to detected characteristics of reflected light;

vii) a lens for focusing light emitted by the emitter tip to provide a focal region and an outwardly projecting diverging illuminated region, the lens locating the focal region in the non-disrupted flow region of the catalytic reactor;

viii) the receiver tip having a numerical aperture, which defines an outwardly diverging viewing cone, the numerical aperture of the receiver tip being selected to provide a viewing cone which overlaps a useful portion of the illuminated region and the focal region to define thereby the sensing region, the lens focusing the light at an angle of incidence at the focal region which ensures that incident light reflected by the catalytic particles moving through the focal region is reflected from the sensing region towards and received by the second fibre optic; and ix) a programmable data processing unit connected to the light detector to interpret detected reflected light signals from the sensing region and provide values for particle velocities and particle concentrations.

In accordance with another aspect of the invention, a method for providing a defined sensing region for sensing presence of small particles passing through the sensing region in a catalytic reactor, to provide signal information and determining catalyst particle velocities and particle concentrations in the reactor, comprises:

i) projecting from an optical probe positioned in the reactor, focus monochromatic light from a laser to define a focal region and an outwardly diverging illuminated region beyond the focal region;

ii) establishing an outwardly diverging view region which is extending outwardly in the same direction as the illuminated region;

iii) the view region being established to overlaps a useful portion of the illuminated region to define thereby the sensing region;

iv) the optical probe as positioned in the reactor disrupting flow of phases to define adjacent the probe a flow disrupted region and outwardly beyond the flow disrupted region, a non-disrupted flow region;

v) positioning the view region and the illuminated region relative to one another to define the sensing region including the focal region in the non-disrupted flow region of the reactor.

BRIEF DESCRIPTION OF THE DRAWINGS

Various preferred embodiments of the invention are described with reference to the drawings wherein.

DETAILED DESCRIPTION OF THE PREFERRED EMBODIMENTS

Although various aspects of the invention will be described with reference to sensing movement of catalytic particles through a defined sensing region, it is understood that the optical probe may be used in a variety of other types of particle or object sensing, whether it be for distance measurement, object size, movement of the object, or the like. Furthermore, it is also contemplated that the optic probe may be used in detecting fluorescence emitted by excited molecules, for example in the detection of fluorescence labelled molecules passing through a defined area, where light emitted by the optic probe is of a selected wave length and frequency to excite the fluorescent label to in tun cause a fluorescent emission. The selection of the fluorescent label would be such to ensure that fluorescence is emitted by the label before the molecule has passed through the defined sensing region.

Although the invention in accordance with various aspects of this invention is particularly suited to the detection of small particles, that is, particles having cross sectional dimensions in the range of 50 microns up to 3 mm, it is understood that the system may also be used to sense particles having cross-sectional dimensions of considerably greater than 3 mm and even flat surfaces. In respect of monitoring catalyst particle movements in catalytic reactors, it is understood that the catalyst particles are generally in the range of 60 to 700 microns in cross-sectional size. As to the use of the optical probe for sensing movement of bubbles in a two or three phase catalytic reactor, the bubble cords may be in the range of 2 to 3 mm or higher.

Figure 1:
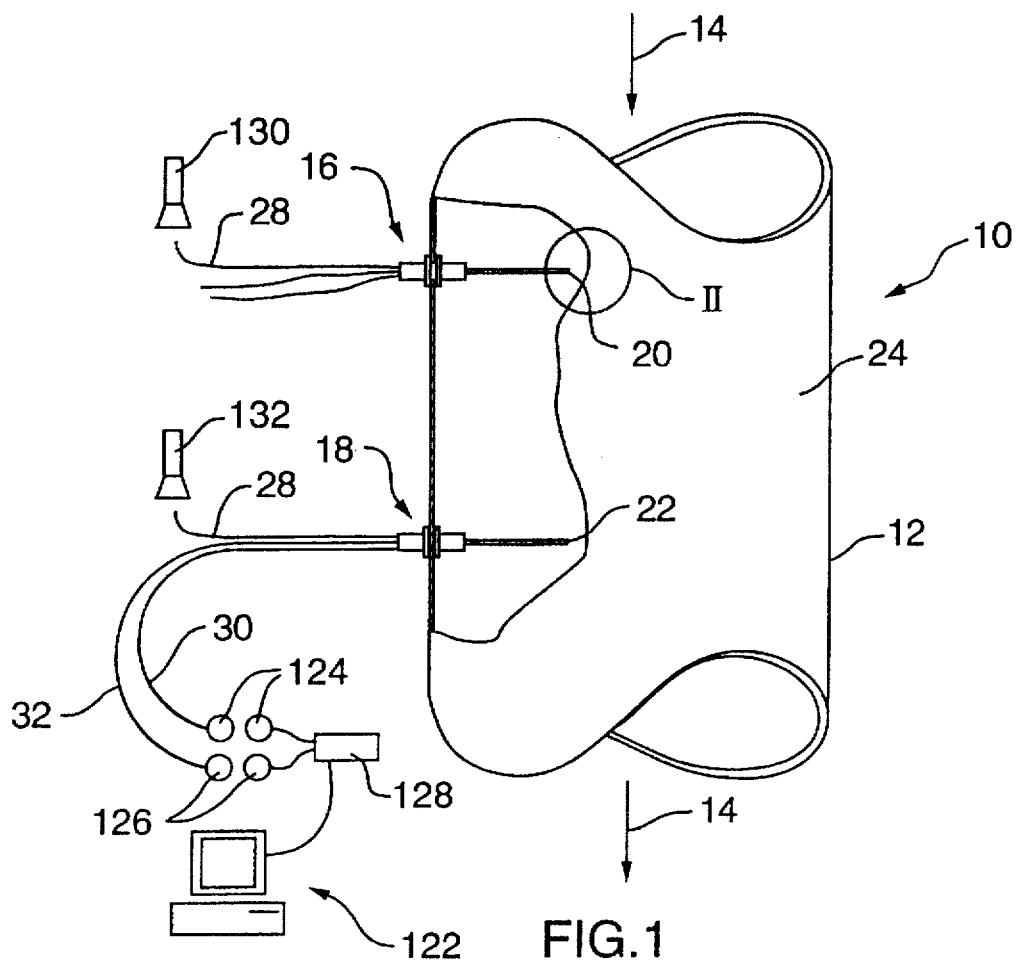
FIG. 1, is a section of a down flow catalytic reactor, having probes in accordance with an embodiment of this invention, mounted therein for detecting characteristics of particle movement.

With reference to FIG. 1, a catalytic reactor 10 is shown having tubular reactor wall 12 with a two or three phase reactant material travelling downwardly in the direction of arrow 14. In accordance with this particular embodiment as illustrated with respect to FIG. 2, the catalytic reactor may have reactants in a gas-solid phase where the reactants in the gas phase are catalyzed over the surface of the small catalytic particles passing downwardly through the reactor 10. In accordance with an aspect of the invention, the movement of the catalytic particles is detected by two separate probes 16 and 18. The probes may be identical, having their respective tips 20 and 22 vertically aligned along the longitudinal direction 24 of the reactor 10. Depending upon the proximity of the probes 16 and 18, it is understood that they need not be positioned one vertically directly beneath the other. Instead, they can be positioned at different circumferential locations about the reactor wall 12. As shown in FIG. 1, the optical probes extend inwardly up the reactor a significant distance. It is understood that the probes however, may be positioned at any desired location in the reactor from the wall 12 through to the central region of the reactor volume.

Several considerations which interrelate with one another to provide various types of optical probes having the features of this invention are required in designing the probe. These considerations are:

a. There should be no unstable regions for the sensor at conditions of maximum light energy in the illuminated region.

b. The detection volume or region of measurement is placed far enough from the sensor tip to mitigate as much as possible the intrusion effects of the sensor on the flow of material through the reactor.

c. Light distribution and so called detection illuminated volume is subject to accurate mathematical modelling and consequently suitable to a mathematical definition using classical optical theories.

d. Configuration and components of the sensor are selected to stand harsh operating conditions involving phenomena such as high corrosion and high temperature, normally encountered in catalytic reactors.

e. The dimensions of the sensor are small enough to be able to be miniaturised and easily mounted and dismounted in large scale catalytic reactors.

In meeting these considerations, the design of the optic probe includes:

a. selecting fibre diameter, b. selecting distance between the tip of the fibre and a focusing lens, and c. selecting diameter and general optical characteristics of the lens to accomplish the specific features of:

i) size of the focal region, and ii) orientation of the incident light in the focal region.

In order to understand these considerations, the particular structure of the optical probe in accordance with two preferred aspects of the invention are described so that the following discussion of the experimental data and mathematical modelling will enable those skilled in the an to use the optical probe system.

Figure 2:
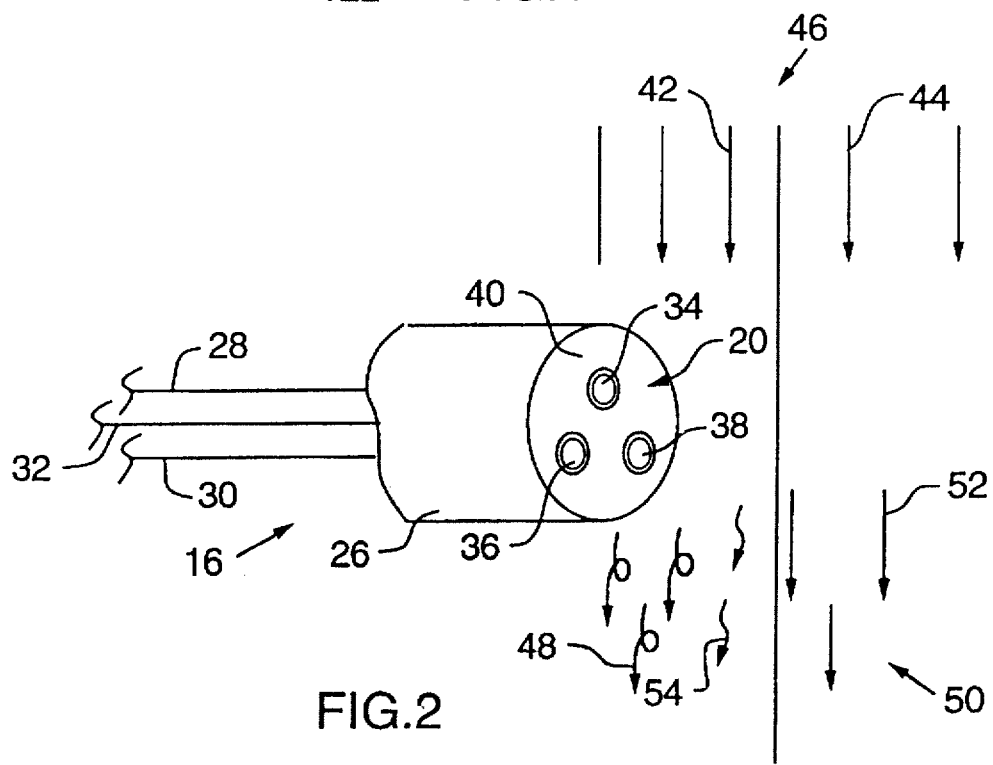
FIG. 2, is the enlarged view of region II of FIG. 1 at the end of the optic probe.

As shown in FIG. 2, the positioning of the probe 16, having a structural enclosure 26 which defines the tip 20 where the optical probe includes an emitter fibre optic 28 and two receptor fibre optics 30 and 32. The lens 34 which focuses the light from the emitter fibre optic 28 is mounted flush with the exterior of the probe tip 20. The two receptor fibres and 32, have their receptor tips 36 and 38 which are polished and are mounted flush with the tip surface 40 of the probe tip 20. Also as shown in FIG. 2, the downward flow of the reactant phases over the probe enclosure 26, sets up disrupted and non-disrupted regions. Schematically illustrated by arrows 42 and 44 an essentially downward un-disrupted flow is provided. However, in the region generally designated 46, the flow of phases 42 over the tip enclosure 26, induces a disrupted flow region as indicated by the arrows 48 in the region 46. Whereas, outwardly thereof in the region 50, the flow is still non-disrupted as indicated by the arrows 52. As is appreciated in moving axially outwardly from the probe face 40, and as indicated by arrows 54, the extent of disrupted flow slowly dissipates in transition through to the non-disrupted flow region 50. Hence, in meeting the above considerations in design of the optic probe, the lens 34 is selected to provide a focal region for the commencement of the illuminated region in the non-disrupted region of flow generally designated 50 in FIG. 2. For most applications, this will necessitate a focal region located approximately 2 mm up to perhaps 100 mm from the lens with sensing region extending from perhaps 1 mm up to 5 or 6 mm. This may result in the sensing region extending beyond the probe by up to 20 mm.

Figure 3:
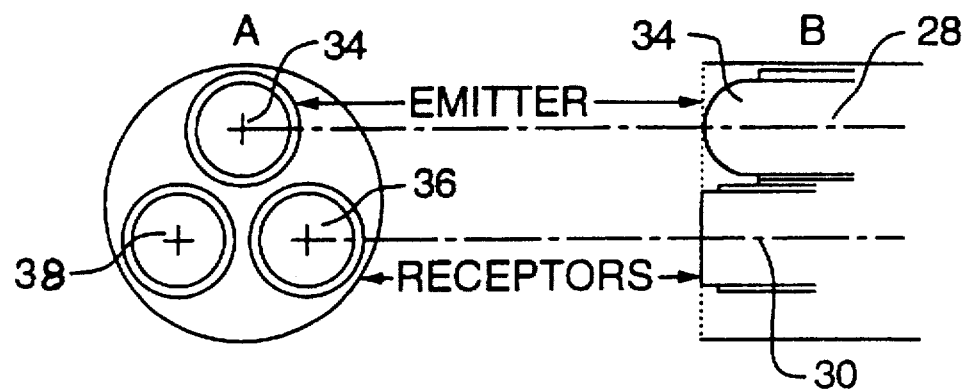
FIGS. 3A and 3B are end and side views of the probe of FIG. 2.
Figure 4:
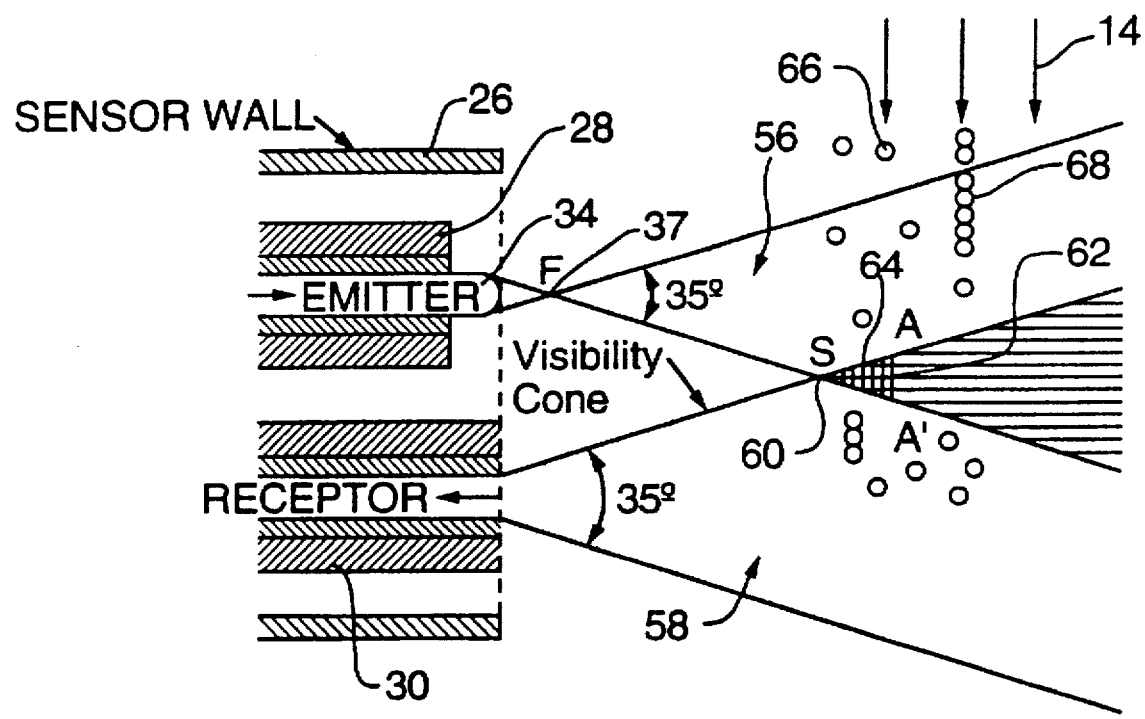
FIG. 4, is a section through the probe of FIG. 1 in accordance with a first embodiment thereof.

With reference to FIG. 3, view A shows the relative position of the lens portion 34 of the emitter fibre relative to the receptor fibre tips 36 and 38. Section B shows the positioning of the emitter fibre 28 relative to the receptor fibre 30. In addition, FIG. 3 shows the integral formation or attachment directly to the emitter fibre 28 of the lens portion 34. As shown in FIG. 4, the sensor enclosure 26 supports the emitter fibre 28 relative to the receptor fibres 30 and 32, where the optics of the emitter and receptor fibres are shown. The integral lens portion 34 of the emitter fibre defines a focal region 37 and an outwardly diverging illuminated region generally designated 56. The angle of divergence for the illuminated region is approximately 35°. A similar angle of divergence of 35° is provided for the viewing region 58 of receptor 30. The divergent angle for the viewing region is determined by the numerical aperture of the receptor fibre. The numerical aperture is selected to ensure that the viewing region 58 intersects and includes a useful portion of the illuminated region 56. As shown in FIG. 4, the viewing cone 58 intersects the illuminated region 56 at juncture 60, where the useful portion of the illuminated region is defined by the line 62. The line 62 is determined by the intensity in this portion of the illuminated region. It is understood that as the intensity falls off in the illuminated region, a point is reached where light reflected by particles in that region is not sufficient to be received quantitatively by the receptor fibre. As will be described in more detail with respect to FIG. 13, the extent of that region can be quantified. In any event, the sensing region then becomes the useful portion 64 of the illuminated region. Hence, any particles passing through this defined region, will reflect light which will be received by the receptor fibre 30 and in turn transmitted to a suitable detector to develop a signal indicative of the presence of the particle. As shown in FIG. 4, the individual particles designated 66 may travel downwardly in the direction of arrow 14. either individually or in clusters as shown at 68. Hence, either the individual particles or agglomeration of the particles due to the slip streaming effect as they travel downwardly, will reflect light from the illuminated region as they travel through the sensing region 64. As demonstrated in FIG. 4, by an appropriate selection of the lens geometry and the numerical aperture for the receptor tip of the fibre, a specifically defined sensing region 64 can be determined. By knowing the exact position of this sensing region and its volume, the particle velocity and particle concentration may be calculated.

It is generally understood that catalytic particles as they move through the flowing region, tend to form strands due to inter-particle and fluid dynamic forces. The agglomeration of the particles into strands is generally thought to be caused in part by the tendencies of the particles to travel in the wake of other flowing particles thereby reducing overall drag of the moving stream of particles. Furthermore, as the concentration of the particles increase in the fluid stream, there is understood to be an increase in the strands of particles. The extent to which strands of particles are being formed is important to the understanding and optimisation of catalytic processes. By suitable mathematical modelling and parameter selection in detecting light signals from particles travelling through the sensing region, an assessment of particle velocity and concentration can be achieved. In accordance with a preferred aspect of the invention, the optical sensor can be designed to measure particle velocities where the superficial gas velocity in the down flow reactor may be in the range of 0.5 to 2.5 m/second, average strand velocity is 0.6 to 3.9 m/second, average strand length is 98 to 583 µm and solids hold up in the range of 0.2 to 0.7% by volume. The mathematical modelling used to analyze the signals from the fibre optic receptors may vary depending upon the types of particles to be sensed as well as the phases in which the probes are positioned. An exemplary form of modelling to obtain information in respect of particle velocity and particle concentration is described in applicant's paper Sobocinski et al., (1995) "New Fibre-Optic Method for Measuring Velocities of Strands and Solid Hold Up in Gas-Solids Down Flow Reactors", Powder Technology 83 (1995), page 1–11, the subject matter of which is incorporated herein by reference. The modelling technique is not considered to be part of this invention, since one skilled in the art may have a variety of techniques for performing a standard form of regressional analysis on the signals from the optical probe in determining characteristics of particles moving through the sensing region.

In accordance with a first embodiment, the lens 34 as provided at the end of the emitter tip, may be integrally formed with the fibre or may be fastened directly to the fibre end. Preferably the lens 34 is formed integrally with the fibre to provide a desired focal region 37, outwardly of which the focused radiant energy diverges to provide an illuminated region. The selected numerical aperture for the receptor is made to position the sensing region 68 in the non-disturbed flow region 50 as shown in FIG. 2. Depending upon the selection of the type of lens 34, it is understood that the focal region 37 may be moved further outwardly axially from the lens to position the focal region 37 in the non-disturbed flow region 50 of FIG. 2.

Figure 5:
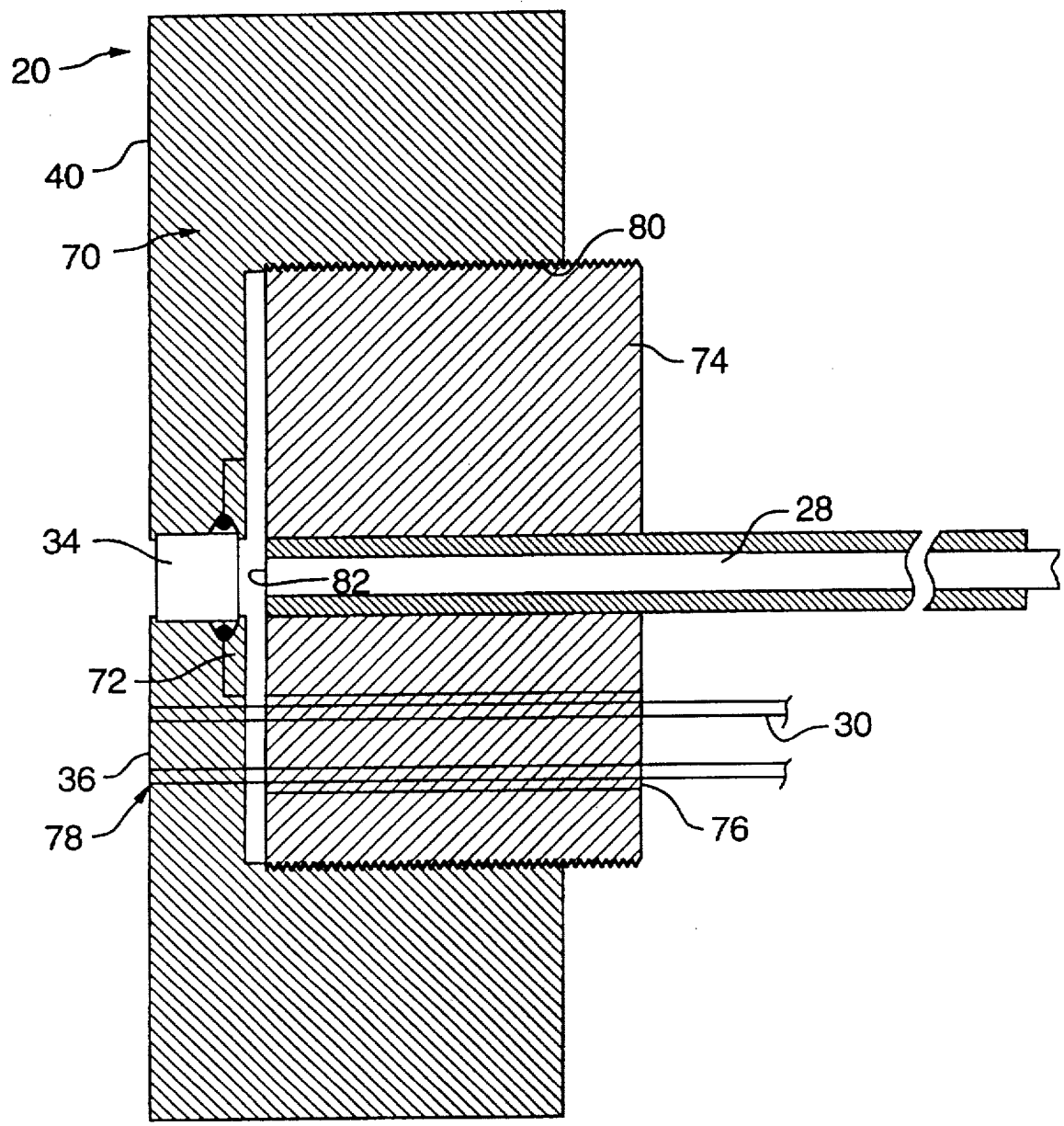
FIG. 5, is a section through the probe in accordance with a second embodiment thereof.

In order to achieve the positioning of the focal region in the non-disturbed flow region of the catalytic reactor, it has been found in accordance with a second embodiment, that a lens spaced from the emitter tip is more effective. However, in order to meet the previously described considerations, the lens must have characteristics which are considerably different from the prior art type of lenses used in focusing light to provide an illuminated region for position sensing. The lens has to be sufficiently small to provide for miniaturisation. In FIG. 5, the probe tip 20 having a probe face 40 is of an overall diameter of approximately 20 mm. The lens for focusing the emitted radiation is preferably in the range of 2 mm diameter. The lens 34 is mounted in the body portion 70 of the probe 20 and is appropriately secured in place by lens retainer 72. The emitter fibre optic 28 is mounted in a threaded collar 74, which has a slot 76 provided therein to accommodate the receptor fibre 30 which extends through the collar 74 and is positioned in the body portion 70 of the probe through an appropriate bore 78 of the probe 20. The threaded collar 74 engages the threads 80 of the body portion 70 of the probe 20, where the threaded collar 74 may be rotated through the distance of the slot 76 to allow movement of the fibre optic emitter tip 82 relative to the lens 34. Such an arrangement produces significant advantages over the system provided in FIG. 4 which will become apparent in the following discussion of the data shown in the various Figures.

Figure 6:
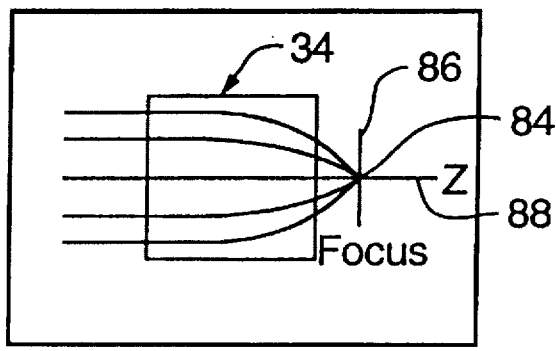
FIG. 6, is a schematic view of the focusing function of a gradient-index (GRIN) lens.

It is understood that the intensity of the illumination emitted from the emitter fibre optic 28 is determined by the power of the radiant energy source which is preferably a laser emitting monochromatic light at a desired wavelength. Although there are available very powerful lasers, it is uneconomical to use very high intensity high power lasers with this type of optical probe system. Instead, it is preferred to use lower intensity lasers, for example, a 15 milliwatt helium-neon laser which emits radiant energy in the infrared region. In order to provide a proper, well defined, sensing region, in which light intensity is sufficient to illuminate particles in the sensing region, one cannot provide a focal region in the range described for example in U.S. Pat. No. 3,940,608, which at least 0.4 inches and possibly up to 5 inches. This may be acceptable when detection in clear air is required and the surface to be sensed is a large planar reflective surface, positioned normally at the focal region. However, that system will not work when sensing catalytic particle position because of the need to illuminate the small particles causing reflection which can be received and transmitted by the receptor. This can only be achieved by providing a well defined sensing region which is sufficiently close to the probe to provide the necessary intensity of illumination in the sensing region, but at the same time, position the sensing region in the non-disturbed flow region of the reactor. A suitable lens which achieves these desired features is a gradient-index (GRIN) lens. This lens has normally been used to focus light in coupling ends of fibre optic to provide continuity in transmitted light energy. It has been determined however, that the GRIN lens melts the above considerations in providing the desired focal region for the sensing region of the optic probe of this invention. The preferred lens 34 as positioned in the probe 20 as shown in FIG. 5 is the GRIN lens. The GRIN lens functions as shown in FIG. 6, where incoming radiant energy, such as in the infra red spectrum and which has been emitted by the tip of the fibre optic 82, is concentrated or focused through the lens 34 to provide a focal region 84 which is disposed generally in the focal plane 86 and set at about the focal axis 88.

Figure 7:
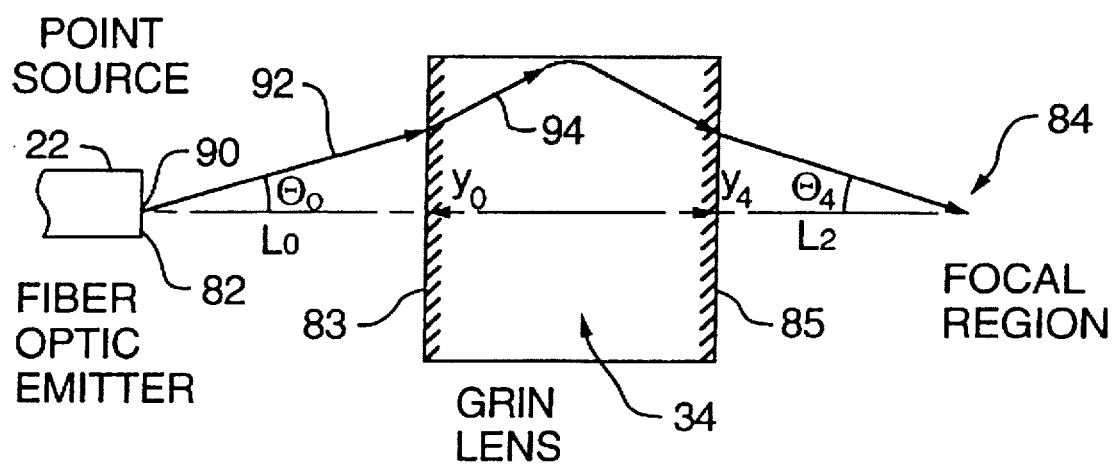
FIG. 7, is a schematic of a point source of radiant energy being focused by the GRIN lens of FIG. 6.

The GRIN lens 34 as shown in FIG. 7, provides for mathematical analysis of the optics, while at the same time, providing the miniaturisation desired such as shown in FIG. 5, with a lens of approximately 2 mm in diameter. The tip face 82 of the emitter fibre optic 22, provides divergent radiant energy such as theoretically exemplified by the point source 90 which has a light ray 92. The light ray 92, is directed towards the focal region 84 by special characteristics of the GRIN lens which curves the light as it enters from the lens incident face 83 internally of the lens to direct the light ray from the lens focusing face 85 towards the focal region 84. Preferred source for the GRIN lens is that sold under the trade-mark "SELFOC" and is identified as the "SELFOC" GRIN. "SELFOC" is a trade-mark to identify a range of lenses made by NSG America Inc. The "SELFOC" GRIN lens may be provided in a variety of selected pitches to define the focal region, as well as, other readily identifiable characteristics to, in particular, define the focal region in the manner required and as described with respect to FIG. 2. Detailed equations are provided in the following examples to demonstrate the manner in which the focal region may be calculated in conjunction with specific parameters given for the GRIN lens and the operation of the optical probe. Although preferably the focal region is at least 2 mm from the lens and extends for up to 2 mm with sensing region perhaps being in the foreground of the focal region as well as that of the focal region.

Figure 8:
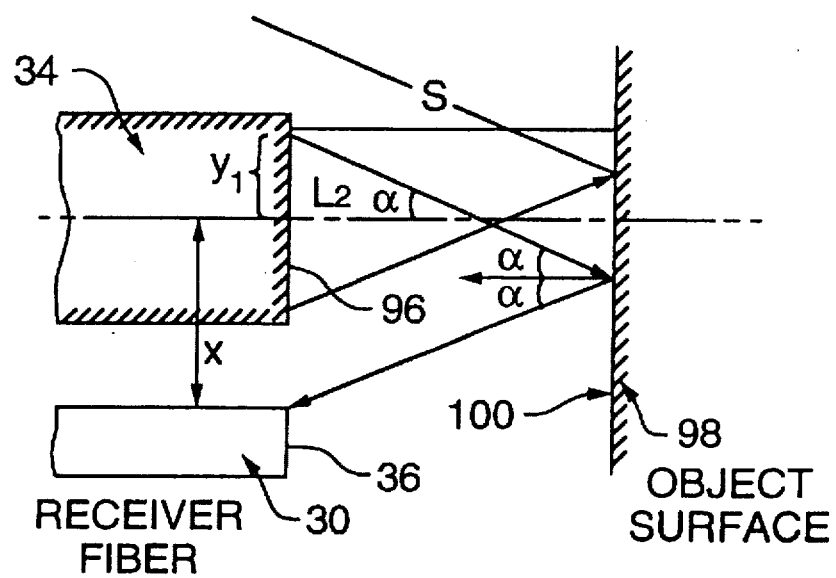
FIG. 8, is a schematic of the receptor fibre relative to the emitter fibre where light reflected is received by the receptor fibre.

In addition to the calculations which may be conducted in determining the focal region, it is also understood that in accordance with FIG. 8, a bench rig may be set up to determine the size and operability of the sensing region. The GRIN lens 34, which schematically is shown to have a diameter approximately twice the diameter of the receptor fibre optic 30, has its face portion 96 positioned in a plane defined by the receptor tip 36 of receptor fibre 30. A solid object 98 may be located on the bench rig to provide a reflective surface 100 which is essentially parallel to the plane in which the GRIN lens face 96 and receptor tip 36 lie. The object surface may be set on a calliberated carrier so as to move the surface inwardly and outwardly relative to the GRIN lens 96. In so moving the reflective surface 100, the intensity of light received by the receptor fibre may be detected and plotted as detected intensity versus distance of the reflective surface from the lens. In respect of a particular bench set up, the results are discussed in respect of to FIG. 18.

FIGS. 9 through 12, illustrate schematically, the geometries of the illuminated region and the viewing region, where the calculations are based on the preferred optical characteristics of the lens for the emitter fibre and for the receptor fibre. However, it is appreciated that the lens may have a half angle of 10° in a thin spherical lens and the receptor fibre may have a numerical aperature of about 10 degrees or greater.

Figure 9:
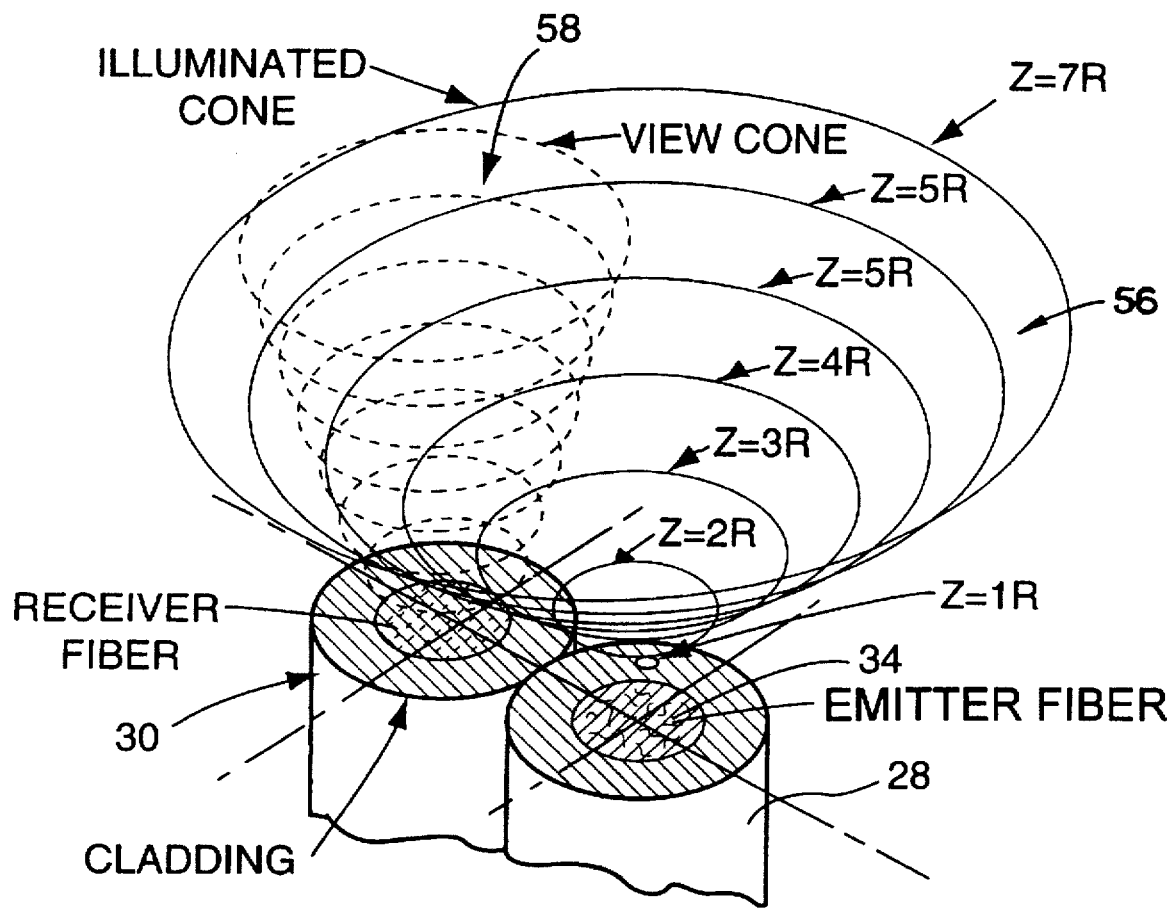
FIG. 9, is a three dimensional schematic of the illuminated region from an emitter fibre having a half angle emitter cone lens of 48.19° and a receptor having a numerical aperture of 15.82° to define thereby the viewing cone.
Figure 10:
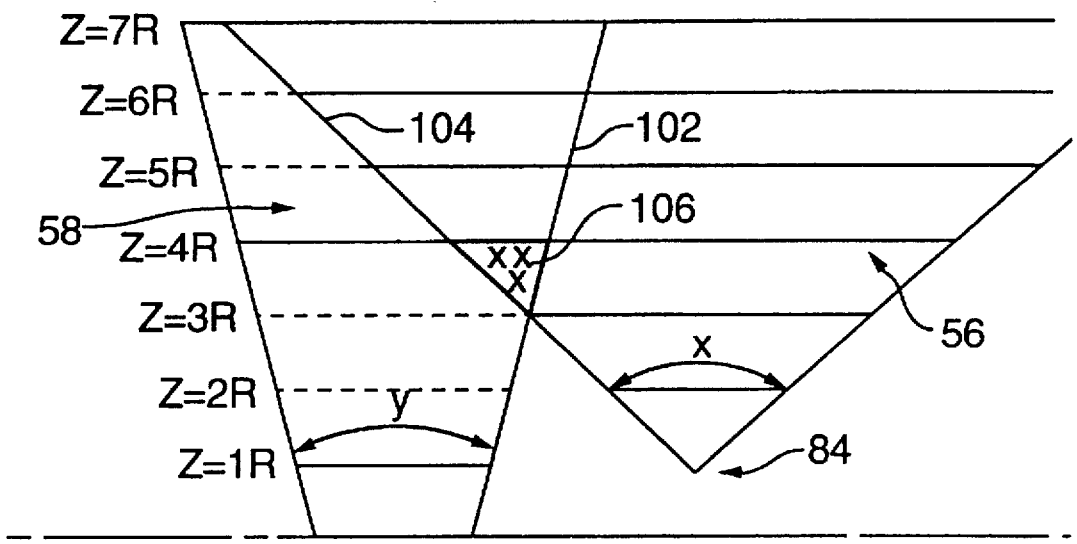
FIG. 10, is a section through the illuminated region and viewing region of the emitter and receptor fibres of FIG. 9.

In respect of FIG. 9, a schematic representation is shown where the emitter fibre has a lens with the equivalent half angle of 43.19°. That lens may be formed by rounding the end of the fibre optic probe to achieve an emitter of the type shown in FIG. 4. The receptor fibre has a numerical aperture of 15.82°. The illuminated region which is in fine shape of a cone is generally designated 56, where the rings of the illuminated region identify distances from the emitter lens by virtue of two times the radius of the lens. The distance is designated Z, where the focal region is at Z=1R and for each ring above that, Z increases by one radius. Similarly, the viewing region 58 is identified by a plurality of rings to define in essence a viewing cone. The rings similarly are identified as being spaced from the receptor tip by a distance equal to a multiple of the fibre radius. The corresponding section through the illuminated region and the viewing cone, is shown in FIG. 10, where the focal region 84 is at Z=1R. The illuminated region 56 has an included angle X which is considerably greater than the included angle Y of the viewing region 58. Based on these particular optical parameters for the emitter and receptor, the sensing region is defined by boundary lines 102 and 104 of the illuminated cone and the viewing core. The effective sensing region for sensing the smaller particles is generally designated 106 in view of decreasing intensity as the object moves further into the region defined by boundary lines 102 and 104. Such decrease in intensity shall be described in respect of the graph of FIG. 13.

Figure 12:
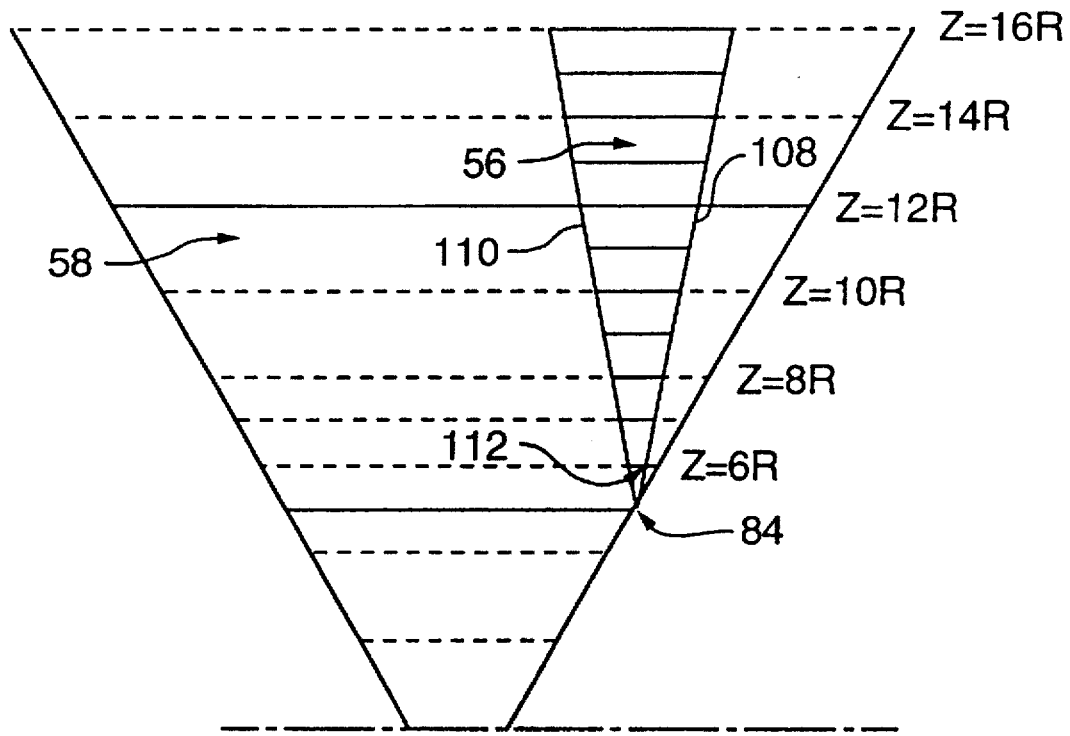
FIG. 12, is a section through the illuminated region and the viewing cone of FIG. 11.
Figure 11:
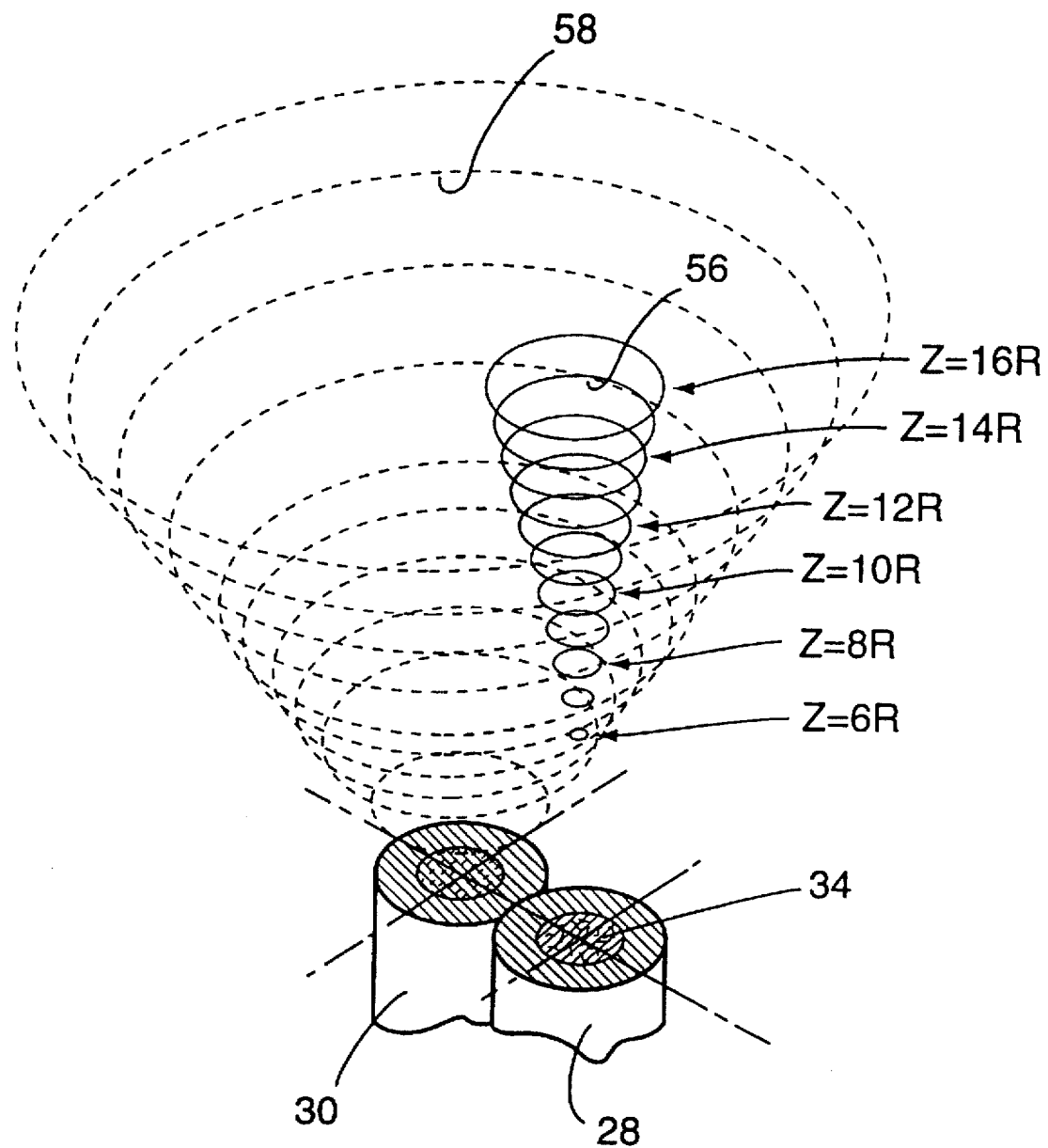
FIG. 11, is a schematic of the illuminated region and the viewing region of an emitter fibre having a half angle of the emitter cone thin lens of 10.86° and a numerical aperture for the receptor fibre of 30°.

In FIGS. 11 and 12, different optical parameters are selected for the lens and for the receptor fibre. The lens has a half angle equal to 10.86° and the receptor fibre has a numerical aperture of 30°. With the relative positioning of the emitter fibre to the receptor fibre, this locates essentially all of the illuminated region 56 within the viewing cone 58 as shown most clearly in FIG. 12. The boundary of the viewing cone 58 intersects the focal region 84 for the illuminated region and includes all of the illuminated region 56. Hence, the sensing region is defined by boundary lines 108 and 110 of the illuminated core, where the lens used has located the focal region approximately 5 times the radius of the emitter fibre. Depending upon the fall off of intensity in the illuminated region, the sensing region is then generally defined within area 112.

As demonstrated by the embodiments of FIGS. 9 through 12, the focal region, by use of particular parameters for the emitter lens and the receptor fibre, may be located a significant distance from the emitter lens and essentially in the non-disturbed flow region as discussed with respect to FIG. 2. Furthermore, by selecting suitable light intensity, the size of the sensing region 106 or 112, may be defined to ensure a sufficient sensing volume to detect the small particles flowing through the sensing region. Furthermore, the shape of the sensing region can also be better defined by the selection of the lens. It has been found that with the GRIN lens, the shape of the sensing region becomes more of a caustic shape than a cone shape. This shape somewhat resembles a flattened cone, having in the direction of particle travel, a thinner sensing region than in the direction laterally of the direction of particle travel of the particles to be sensed.

Figure 13:
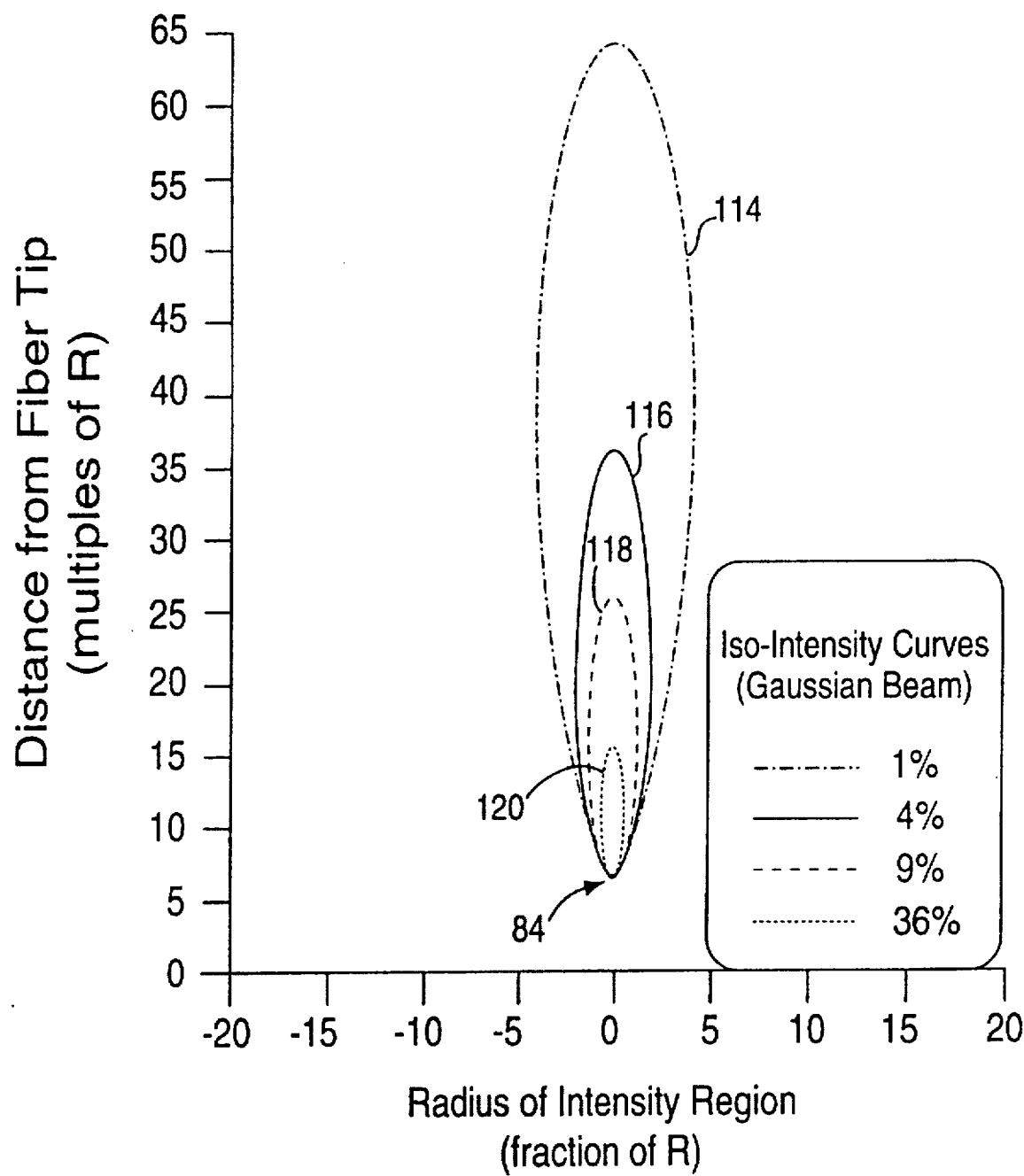
FIG. 13, is a graph showing the intensity of illumination in the illuminated region of FIG. 12.

In defining the shape and size of the sensing region, consideration has to be given to the intensity of illumination in the illuminated region. This is best demonstrated with respect to FIG. 13, where intensity is reported as a function of distance from the lens focusing face 85 as well as distance laterally of the axis for the illuminated region. This results in a plot as shown in FIG. 13, where the various iso-intensity curves are shown ranging from intensity of 1% of the incident radiation as curve 114, 4% as curve 116, 9% as curve 118 and 36% is curve 120. In order to provide for a reliable sensing of small particles moving through the sensing region, it is understood that the intensity of the sensing region should be well above 36% of the incident radiation, hence defining within curve 120 a sensing region considerably smaller and including the focal region 84. Furthermore, the lateral distance that is radially outwardly of the axis of the illuminated region, the distance becomes progressively smaller until the sensing region is in the range of having a overall width dimension of ≦1R up to + or −2R. As described with respect of FIGS. 9 through 12, the boundary of the sensing region is defined and the depth of the sensing region is determined in accordance with light intensity, whereas described and shown in FIG. 13, the depth of the field is based on the calculated intensity knowing the medium through which the light travels as well as its instant intensity. By virtue of these parameters, the size of the sensing region is determined to then assist in the calculation carried out by a conventional processing unit 122 of FIG. 1, which received input from the two receptor optic fibres of the at least one optic probe. The two receptor fibres 30 and 32 transmit light reflected by particles moving downwardly of the reactor, to photo-optic detectors 124 and 126. The signals from the photo-optic detectors are transmitted to a suitable amplifier 128, which in turn, transmits the signal information to the processing unit 122 to perform the necessary regression analysis on the data to provide values for particle velocities and particle concentrations. Also as shown in respect of FIG. 1, representative lasers 130 and 132 are provided for the emitter fibre 28 of each probe.

FIGS. 14 through 17 provide for two selected optic parameters of the GRIN lens, the indication of the highest intensity for distance between the lens and the emitter tip as well as the lateral intensity for each sensing region. The data for FIGS. 14 through 17 is compiled by use of a GRIN lens set up shown in FIG. 5, only the receptor fibre 30 is not used, instead, the receptor fibre is located outwardly of the GRIN lens and either position axially align with the GRIN lens or offset therefrom, depending upon the measurements being taken.

Figure 14:
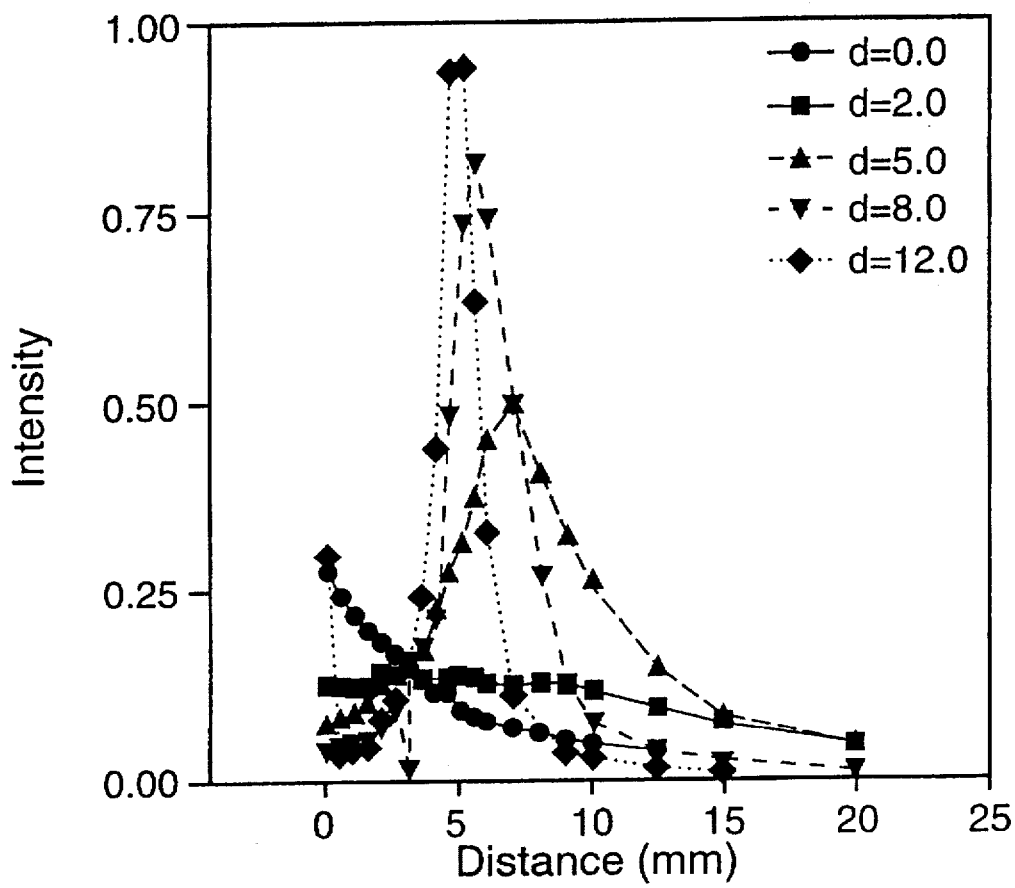
FIG. 14, is a graph showing the distribution of light intensity with axial distance between emitter tip and the lens.
Figure 15:
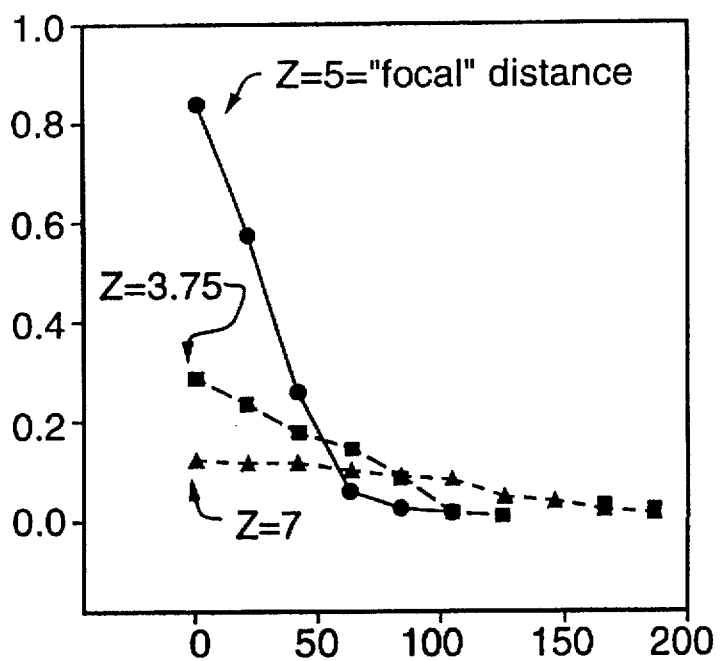
FIG. 15, is a graph showing the distribution of light intensity for various sections through the illuminated region at various distances between emitter tip and the lens.
Figure 16:
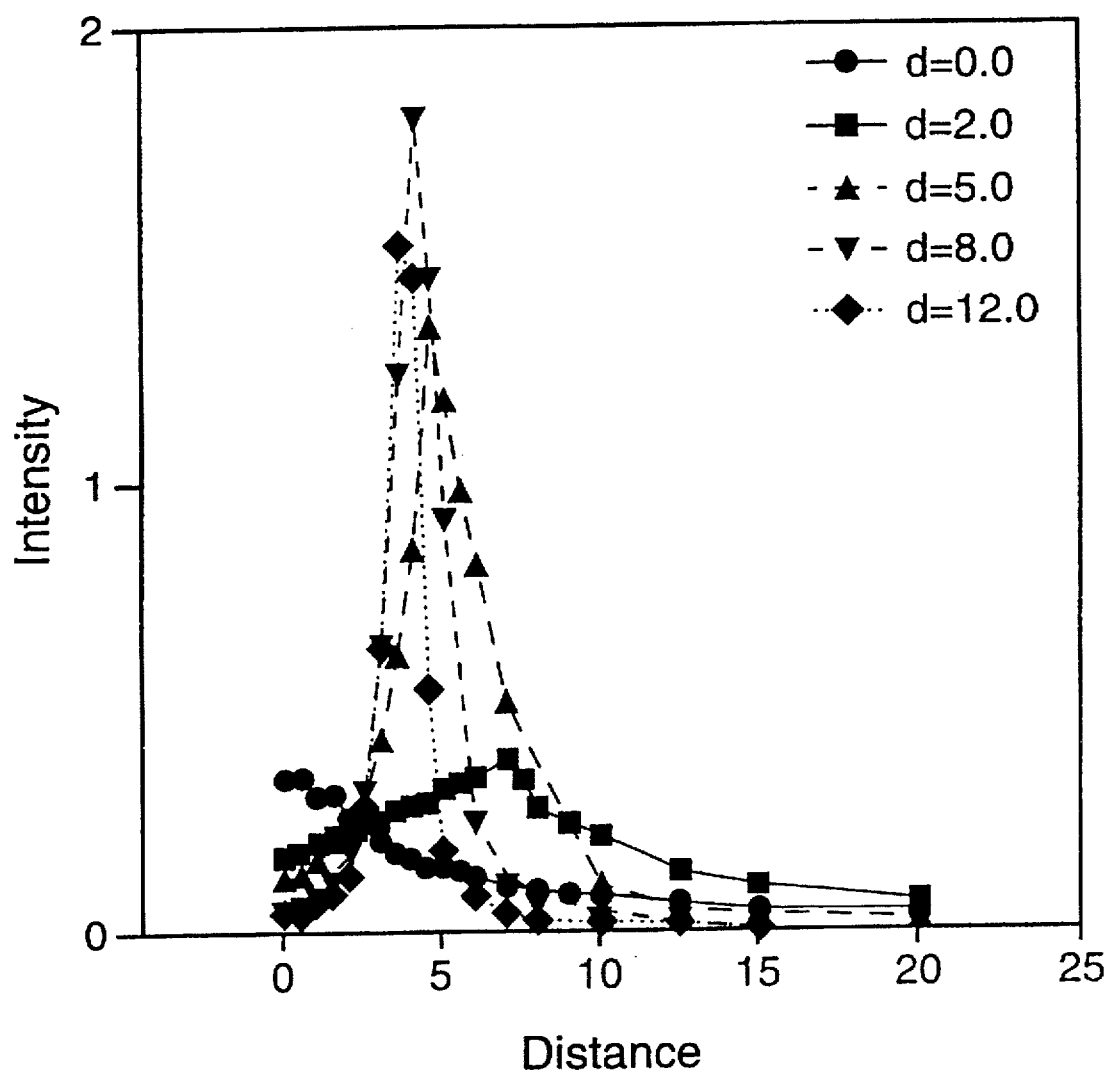
FIG. 16, is a graph showing the distribution of light intensity with axial distance between emitter tip and the lens referencing a different embodiment of the lens.
Figure 17:
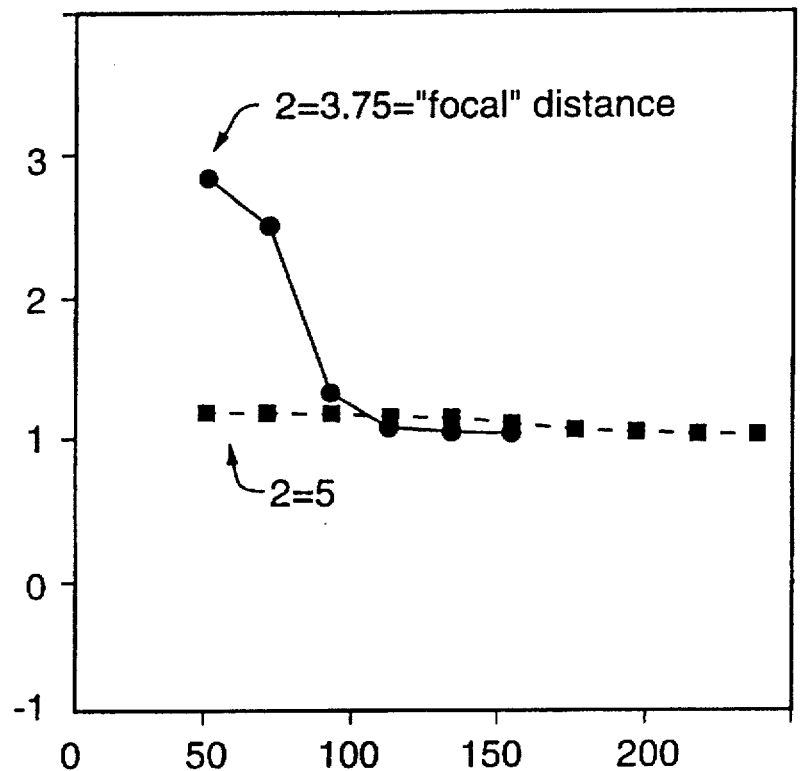
FIG. 17, is a graph showing the distribution of light intensity for various sections through the illuminated region at various distances between emitter tip and the lens referencing a different embodiment of the lens.

FIG. 14 is a plot of intensity versus the distance of the receptor tip from the lens. The various plots represent various distances between the lens and the fibre optic tip. As described with respect of FIG. 5, that distance may be varied by rotating the body portion 74 to thereby move the emitter tip face 82 relative to the lens face 83. The various distances between the emitter tip face 82 and the lens incident 83 are described on the graph as d=0 up to 12 mm, where the various intermediate distances are noted and identified on the graph by the indicated markers. The GRIN lens has a pitch of 0.08 where a pitch of 1.0 describes the length of a GRIN lens needed for a light of a certain wave length to execute one cycle or one sign wave within the lens. Hence the pitch of the lens is selected based on the wave length of the incident light and the desired positioning of the focal region. It is apparent from FIG. 14 that with d, the separation between the emitter tip and the lens equal to either 8 or 12 mm, the greatest intensity of light received by the emitter tip, positioned axially outwardly from the lens is around 4.5 to 5.5 mm. At this highest intensity, it is apparent that the focal region and slightly to either side thereof, defines the best location for the sensing region. As shown in FIG. 15, for d=12 mm and the GRIN lens having 0.08 pitch, the intensity laterally of the sensing region at various distances from the lens surface is indicated by Z being a number in millimeters. It is apparent that where Z=5 mm, that is in the focal region, the intensity laterally of the axis falls off slowly until the receptor fibre is moved to a laterally displaced position of about 50 microns. It is noted that the initial intensity axially of the lens is of course at the highest value of 0.8 units. At a distance 7 mm from the lens, the intensity where Z=7, is equal to 0.1 unit or less which indicates the inutility of that region. Correspondingly, in front of the focal region for Z=3.75 mm, the intensity at zero laterally displayed distance is 0.3 units which falls off below the intensity at Z=5 mm at an axial distance of 50 microns. A similar realization is provided in FIGS. 15 and 17. As shown in FIG. 16, the results for intensity versus distance from the lens for the receptor fibre is carried out for a GRIN lens having a pitch of 0.1 with various distances d=0 through 12 mm. The focal region is in the range of about 3.5 to 5 mm, depending upon the value for d. When d is 12 mm as shown in FIG. 17, the intensity is greatest in the various axial positions, when Z=3.75 mm which is the focal region for d=12 of FIG. 16. When the emitter fibre is positioned at Z=5 mm, it is apparent that the intensity has fallen off close to zero, thereby rendering that portion of the sensing region useless for detecting presence of small particles moving there through.

It is apparent from the graphs set out in FIGS. 14 through 17, that the characteristics of the optical probe, depending upon the selection of the optical parameters for the lens and the receptor fibre, can be determined so that the shape and size of the sensing region can also be well defined. It is also apparent that by having a mechanism such as in FIG. 5 which allows adjustments of distance between emitter tip and lens, one can readily vary the focal region shape and location to achieve with a single unit such focal region shaping to suit a particular need in sensing particle movement.

Figure 18:
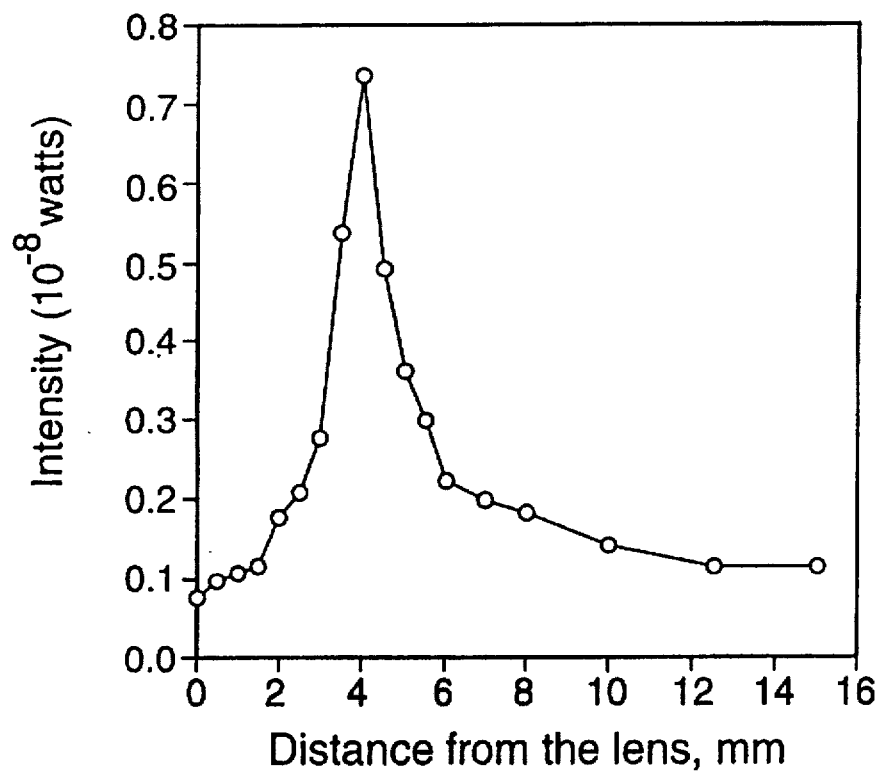
FIG. 18, is a graph showing the intensity of reflected light for an object moving through the sensing region at various axial distance from the lens.

FIGS. 18 illustrates further aspects in considering the design for the optic probe. The lens used in focusing the radiation is designed to minimize the common problem associated with lenses used in the prior art, particularly those described in U.S. Pat. No. 3,940,608 and other related art, where the intensity of the radiation falls essentially to zero for sensing purposes at the focal region. Although this feature is necessary in the prior art form of sensing, it does not work in the system of this invention. Applicant has found that this problem can be avoided as shown in FIG. 18, by selecting a lens which provides a sufficient angle of incidence to reflect light off of particles whether they present a flat or irregular surface, towards the receptor fibre when the particles pass through the focal region of the sensing region. A system similar to FIG. 8, where an object is moved away from the lens and an intensity reading taken from essentially adjacent to the lens through to a considerable distance from the lens. The lens configuration of this invention provides the focal region a sufficient distance from the lens that the sensing region is located in the non-disturbed area of flow, but at the same time not so far from the lens that light in the axial region is reflected directly back to the emitter rather than the receptor tip.

FIG. 18, further demonstrates the results in using the modified device of FIG. 8, where the drop in intensity in the focal region is minimized. The modification is that the object is a 180 micrometer wire which presents a slightly curved surface when compared to the size of the fibre optic. As shown for a focal region of about 4.5 mm, the intensity is greatest in the range of 0.7 units. Considering that an intensity of about $\leq 0.3$ units in the sensing region is below the useful level of intensity, the sensing region as shown in FIG. 18 extends from about 3.5 mm from the lens to about 5.5 mm from the lens. In this region of course, is located the focal region where as demonstrated with respect to these particular parameters for the lens, the sensing region may include a small portion of the fore region of the focal region and as well a portion aft of the focal region.

In order to further assist one skilled in the art in selecting the lens parameter, the following equations are provided in calculating the various characteristics of the probe based on the exemplary parameters given.

Basic Design Equations Used in the Design of CREC-GS-Optiprobe. Sample of Calculation
1. Rays emitted in a Point Source and reaching a Grin Lens from air media.

Rays reach the Grin lens interface following the Snell Law as:

$$n_{air} \sin [\theta_o] = n_o \sin [\theta_1] \tag{1}$$

Thus, for rays reaching the Grin lens interface from air media ($n_{air}=1$) the previous equation can be approximated (paraxial approximation) as:

$$\theta_o = \theta_1 n_o \tag{2}$$

or $$\theta_1 = \theta_o/n_o \tag{3}$$

2. Refractive Index Distribution in a Grin Lens $$n(r) = n_o (1 - A/2 \, r^2) \tag{4}$$

with r=radial coordinate in the Grin lens (mm)
$n_o$=refraction index of GRIN lens at r=0
A=grin lens gradient constant (1/mm$^2$)

3. Rays equations in a Grin Lens: Incoming Point (Grin Lens Side)

$$y(z) = R_o \sin[\sqrt{A} \, z + \delta] \tag{5}$$

and $$\theta(z) = \sqrt{A} \, R_o \cos[\sqrt{A} \, z + \delta] \tag{6}$$

where z=axial coordinate in the Grin Lens (mm)
$R_o$=maximum rays deviation from centerline (mm)
$\delta$=phase shift determine by a position and direction of incident ray Combining eqs (3), (5) and (6) with $\theta(z)$ and $y(z)$ calculated at z=0, the following relationships result for $R_o$ and $\delta$:

$$R_o = \sqrt{y_o^2 \frac{\theta_o}{n_o^2} A} \tag{7}$$

and $$\delta = \arctan \left[ \frac{y_o n_o \sqrt{A}}{\theta_o} \right] \tag{8}$$

4. Rays in the Grin Lens-Radius of Acceptance and Height of the Pupil ($y_0$)

A Grin lens of radius R will only accept those rays with $R_o <= R$. Thus, the extreme rays touching the edge of the lens must have starting values that satisfy the following:

$$R = \sqrt{y_o^2 + \frac{\theta_o}{n_o^2 A}} \tag{9}$$

As well, rays evolving in the region before reaching the lens with initial deviation of $\theta_o$ direction will require a $L_1$ distance to entry the Grin lens at a $y_o$ height:

$$\theta_o = \tan [\theta_o] = [y_o/L_1] \tag{10}$$

Thus, $$R = \sqrt{y_o^2 \left( 1 + \frac{1}{L_1^2 n_o^2 A} \right)} \tag{11}$$

or as a result it can be shown that the height of the pupil ($y_o$) can be expressed as follows:

$$y_o = \frac{R}{\sqrt{1 + \frac{1}{L_1^2 n_o^2 A}}} \tag{12}$$

5. Rays in the Grin Lens: Outgoing Point (ambient medium side)

Let assume that the Grin Lens has the length L and the pitch P, then $$L = 2\pi P/\sqrt{A} \qquad (13)$$

and as a result the height of the pupil at the outgoing point $(y_1)$ and the angle of this rays can be expressed as:

$$\theta_1 = \theta_o \cos(2\pi P) - y_o n_o \sqrt{A} \sin(2\pi P) \qquad (14)$$

and $$y_1 = \frac{\theta_o \sin(2\pi P)}{n_o \sqrt{A}} + y_o \cos(2\pi P) \qquad (15)$$

6. Evaluation of Focal Distance ($L_2$)

Given that $\tan(\theta_1)$ can be equated with $y_1$ and $L_2$, the focal distance $L_2$ based on the extreme rays can be calculated as:

$$L_2 = \frac{y_1}{\tan\theta_1} \qquad (16)$$

7. Calculation of the Visible Domain for the Receiver

Figure 19:
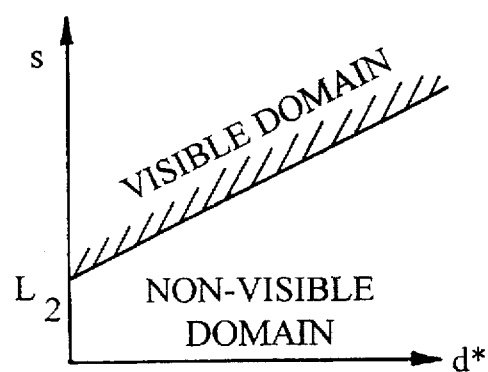
FIG. 19, is a graph showing the visible domain for the receiver.

Geometrical consideration based on FIG. 19 allow to relate the following geometrical parameters:

$$x = (s - L_2)\tan\alpha + s\tan\alpha = (2s - L_2)\tan\alpha \qquad (17)$$

with x=separation between the axis of the emitter and the edge of the receiver. As well given that $\tan\alpha = y_1/L_2$ it results:

$$x = \left(\frac{2s}{L_2} - 1\right) y_1 \qquad (18)$$

Given that the condition of catching light can be expressed by an inequality:

$$x \geq y_1 + d^* \qquad (19)$$

with $d^* = d + (R - y_1)$

Making the appropriate substitutions under the assumptions that the screen reflecting the rays is placed farther than the focal distance it can be concluded that the s critical distance defining the visible domain is given as:

$$s \geq L_2 \left(1 + \frac{d^*}{2y_1}\right) \qquad (20)$$

8. Sample of numerical Calculations and Geometrical Characteristics of GS-CREC-Optiprobe a) Parameters of the Grin Lens used in CREC-GC-Optiprobe $n_o = 1.6075$ $A = 0.092416$ (1/mm$^2$)

$P = 0.1$ $R = 1.0$ mm b) Parameters of the Geometry of GREC-GS-Optiprobe $d = 0.2$ mm c) Additional Geometrical Parameters of GREC-GS-Optiprobe $L_1 = 10$ mm d) Calculation of Rays Characteristics in Grin Lens-Incoming Point (incoming Pupil)

$y_o = 0.98$ mm $\theta_o = 4.51$ degrees e) Calculation of Rays Characteristics in Grin Lens-Outgoing Point (Outgoing Pupil)

$y_1 = 0.91$ mm $\theta_1 = 11.57$ degrees f) Calculations of the Focal Point for the Extreme Rays $L_2 = 4.5$ mm g) Calculation of the Visible domain For a $d^*$ value of 0.3 mm the s parameter is 5.2 mm.

9. Conclusions

This sample calculation demonstrates that a most probable focal point is going to be placed at 4.5 mm. This means that all rays coming from a reflecting object placed at 5.2 mm will be seen by the receiver.

Although preferred embodiments of the invention are described herein in detail, it will be understood by those skilled in the art that variations may be made thereto without departing from the spirit of the invention or the scope of the appended claims.

We claim:

1. An optical probe for sensing presence of small moving particles passing through a defined sensing region, said probe comprising:

i) an emitter optic fibre for transmitting from its tip radiant energy outwardly of said probe;

ii) a receptor optic fibre for receiving radiant energy reflected or emitted by such particles moving through said sensing region;

iii) a lens for focusing radiant energy emitted from said emitter tip into a focal region spaced outwardly of said probe and which radiant energy diverges outwardly from said focal region into a defined high density radiant energy region.

iv) said receptor optic fibre defining a diverging viewing region projecting outwardly towards said high density radiant energy region, said receptor optic fibre being positioned relative to said lens to project said viewing region to overlap a useful portion of said high density radiant energy region to define thereby said sensing region.

2. A probe of claim 1, wherein said viewing region includes at least said focal region whereby said focal region is included in said sensing region, said lens focusing said energy at an angle of incidence at such focal region which provides for such incident radiation being reflected or emitted by particles passing through said focal region, is directed towards and received by said receptor optic fibre.

3. A probe of claim 2 wherein said defined sensing region extends beyond and outwardly of said focal region a range of 10 mm to 20 mm, and said focal region is located by said lens an axial distance outwardly of said lens a minimum of about twice optic fibre diameter beyond the range of up to 10 mm.

4. A probe of claim 2 for sensing particles having a diameter in the range of 0.01 mm to 300 mm.

5. A probe of claim 2 wherein said radiant energy is selected monochromatic light of a laser to provide said high density radiant energy region as an illuminated region.

6. A probe of claim 5 wherein said lens is integral with an emitter tip of said fibre optic.

7. A probe of claim 5 wherein said lens is a gradient-index (GRIN) lens having a selected pitch to define said focal region, said lens being spaced from said emitter tip.

8. An optical probe of claim 7 wherein said GRIN lens provides a focal region of at least about 2 mm from said fibre optic emitter tip.

9. An optical probe of claim 8 wherein means is provided for adjusting distance between said lens and said emitter tip to adjust shape of focal region and/or position of focal region.

10. An optical probe of claim 8 wherein said receptor fibre optic has a numerical aperature of greater than 10° to project said viewing region in the shape of a viewing cone.

11. An optical probe of claim 10, wherein said GRIN lens has a focusing strength equivalent to a spherical lens having a half angle of 10 degrees in a thin spherical lens, a tip of said receptor having a numerical aperature of about 25 degrees whereby all of said illuminated region is included in said viewing cone wherein a perimeter portion of said viewing cone intersects said illuminated region at said focal region.

12. An optical probe of claim 11 wherein said focal region is located axially outwardly of said emitter tip by at least 6 mm.

13. An optical probe of claim 11 wherein said illuminated region is caustic shaped.

14. An apparatus for detecting presence of minute catalytic particles passing through a defined sensing region in a catalytic reactor to determine catalyst particle velocities and particle concentrations in said reactor, said apparatus comprising:

i) an optical probe for sensing catalytic particles passing through said sensing region;

ii) a laser emitting monochromatic light of an energy and wavelength which is reflected by minute catalytic particles in a fluid stream;

iii) a first fibre optic for transmitting said light from said laser to said probe;

iv) a second fibre optic for receiving light reflected by catalytic particles passing through said sensing region;

v) said optical probe when positioned in a catalytic reactor disrupting flow of the reactor phases to define adjacent said probe a flow disrupted region and outwardly beyond said flow disrupted region, a non-disrupted flow region;

vi) said first fibre optic terminating in an emitter tip and said second fibre optic terminating in a receiver tip where said emitter tip is positioned adjacent said receiver tip, said second fibre optic transmitting received reflected light to a light detector which generates signals proportional to detected characteristics of reflected light;

vii) a lens for focusing light emitted by said emitter tip to provide a focal region and an outwardly projecting diverging illuminated region, said lens locating said focal region in such non-disrupted flow region of such catalytic reactor;

viii) said receiver tip having a numerical aperature which defines an outwardly diverging viewing cone, said numerical aperature of said receiver tip being selected to provide a viewing cone which overlaps a useful portion of said illuminated region and said focal region to define thereby said sensing region;

ix) said lens focusing said light at an angle of incidence at said focal region which ensures that incident light reflected by said catalytic particles passing through said focal region is reflected from said sensing region towards and received by said second fibre optic; and x) a programmable data processing unit connected to said light detector to interpret detected reflected light signals from said sensing region and provide values for particle velocities and particle concentrations.

15. An apparatus of claim 14 wherein said lens is integral with said emitter tip.

16. An apparatus of claim 14 wherein said lens is separated from said emitter tip.

17. An apparatus of claim 16 wherein said lens is a gradient-index (GRIN) lens.

18. An apparatus of claim 17 wherein means is provided for adjusting distance between said lens and said emitter tip to adjust shape of focal region and/or position of focal region.

19. An apparatus of claim 17 wherein said GRIN lens provides focal region of at least about 3 fibre optic diameters of said emitter tip.

20. An apparatus of claim 19 wherein said GRIN lens has a focusing power equivalent to a spherical lens having a half angle of 10 degrees, said receiver tip having a numerical aperature of 25 degrees whereby all of said illuminated region is included in said viewing cone.

21. An apparatus of claim 20 wherein said illuminated region is caustic shaped.

22. A method for providing a defined sensing region for sensing presence of small particles passing through said sensing region in a catalytic reactor to provide signal information in determining catalyst particle velocities and particle concentrations in said reactor, said method comprising:

i) projecting from an optical probe positioned in said reactor focused monochromatic light from a laser to define a focal region and an outwardly diverging illuminated region beyond said focal region;

ii) establishing an outwardly diverging view region which is extending outwardly in the same direction as said illuminated region;

iii) said view region being established to include a useful portion of said illuminated region to define thereby said sensing region;

iv) said optical probe as positioned in said reactor disrupting flow of reactor phases to define adjacent said probe a flow disrupted region and outwardly beyond said flow disrupted region, a non-disrupted flow region;

v) positioning said view region and said illuminated region relative to one another to define said sensing region including said focal region in said non-disrupted flow region of said reactor.

23. A method of claim 22 wherein said light is focused by a gradient-index (GRIN) lens.

24. A method of claim 23 wherein said view region is established by use of a fibre optic receiver tip having a selected numerical aperature to define said view region.

25. A method of claim 24 wherein said light is transmitted to said lens by use of a fibre optic having an emitter tip.

26. A method of claim 25 wherein position of said lens relative to said emitter tip is varied as desired to position said focal region in said non-disrupted flow region.

27. A method of claim 24 wherein said emitter tip is positioned adjacent said receiving tip.

* * * * *